United States Patent [19]

Toleman

[11] Patent Number: 5,469,848
[45] Date of Patent: Nov. 28, 1995

[54] TONOMETER

[76] Inventor: Paul Toleman, 6 Denesway, Sale, Manchester, United Kingdom, M33 4PY

[21] Appl. No.: 256,169

[22] Filed: Jul. 8, 1994

[30] Foreign Application Priority Data

| Jan. 11, 1992 | [GB] | United Kingdom | 9200642 |
| May 18, 1992 | [GB] | United Kingdom | 9210584 |
| Jul. 14, 1992 | [GB] | United Kingdom | 9214888 |

[51] Int. Cl.$^6$ ........................................ A61B 8/00
[52] U.S. Cl. ............................. 128/660.02; 128/661.06
[58] Field of Search ..................... 128/645, 661.06, 128/660.02, 748

[56] References Cited

U.S. PATENT DOCUMENTS

| 3,948,248 | 4/1976 | Zuckerman et al. |
| 5,148,807 | 9/1992 | Hsu. |
| 5,251,627 | 10/1993 | Morris .......................... 128/645 |

FOREIGN PATENT DOCUMENTS 536574  4/1993  European Pat. Off. .

*Primary Examiner*—George Manuel
*Attorney, Agent, or Firm*—Salter & Michaelson

[57] ABSTRACT

A tonometer for measuring the Intra-ocular pressure of an eye includes an emitter for emitting a primary signal towards the cornea of the eye, a receiver for receiving the primary signal on being reflected from the cornea, and a monitoring device for monitoring the peak-to-peak amplitude of the reflected primary signal received by the receiver. The monitoring device is capable of taking and/or storing a measurement when the distance between the eye and the receiver is such that substantially the largest peak-to-peak amplitude of the primary reflected signal is received. The measurement is calibrated to provide the Intra-ocular pressure of the eye. A method of monitoring the Intra-ocular pressure of an eye is also disclosed.

6 Claims, 5 Drawing Sheets

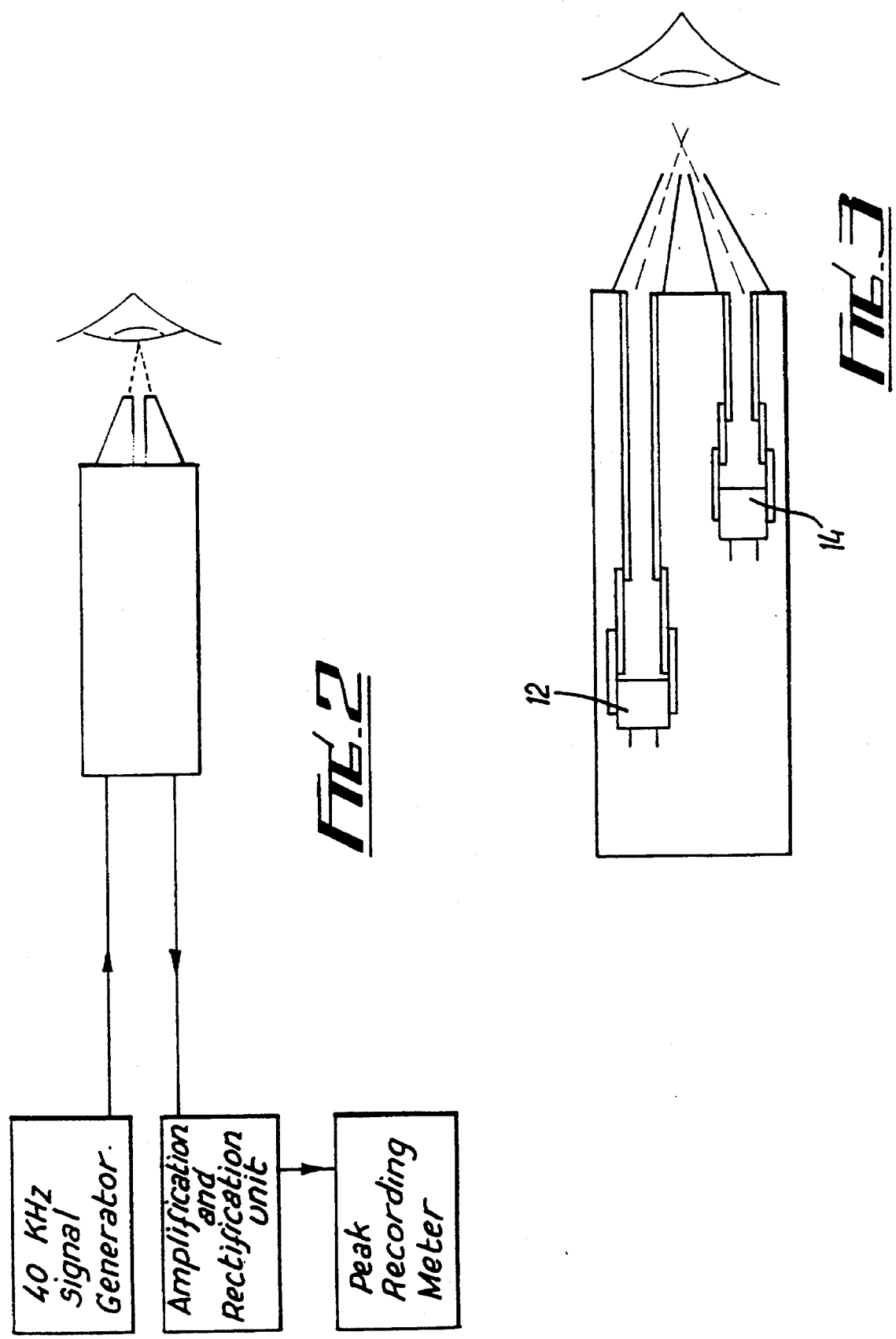

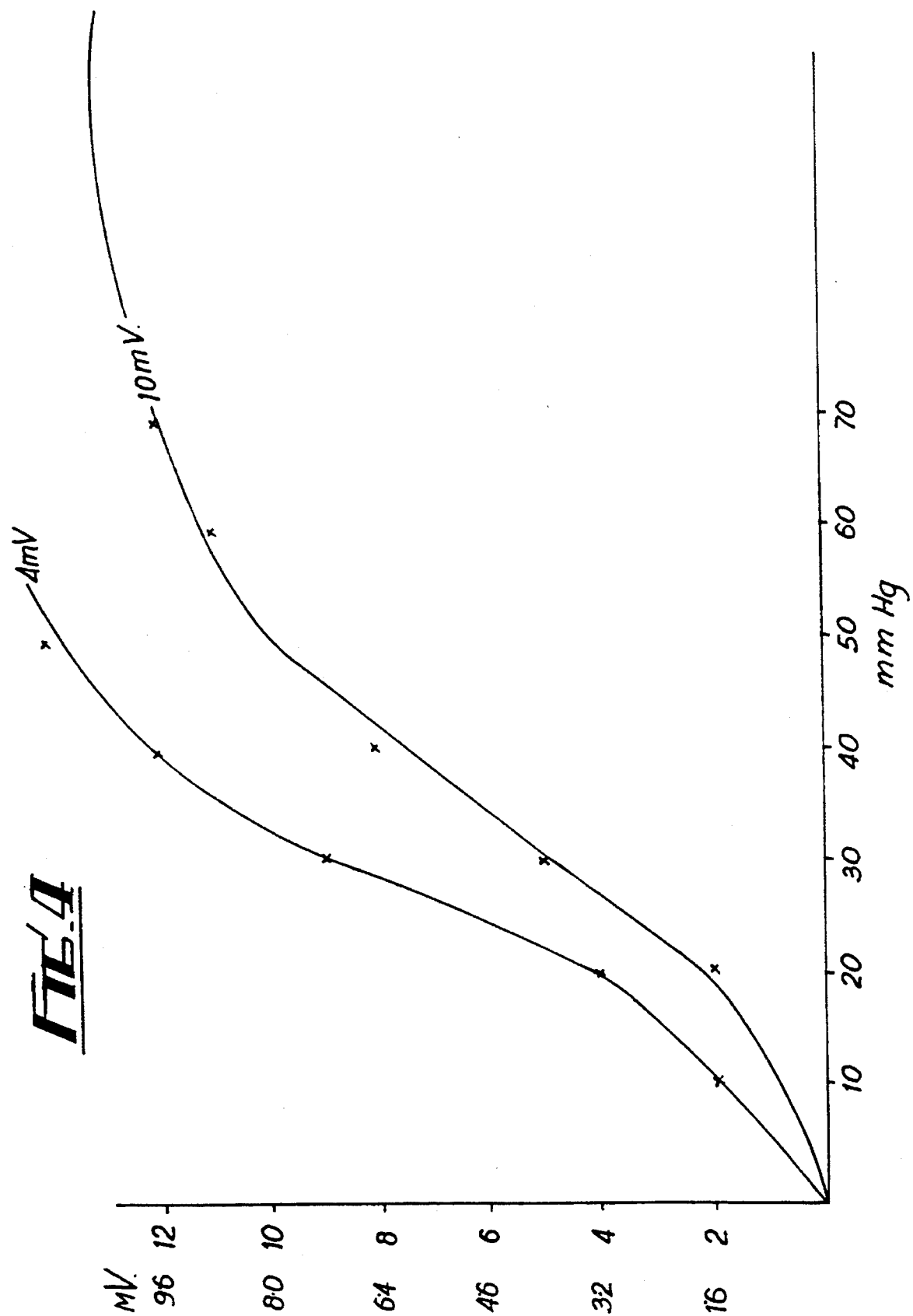

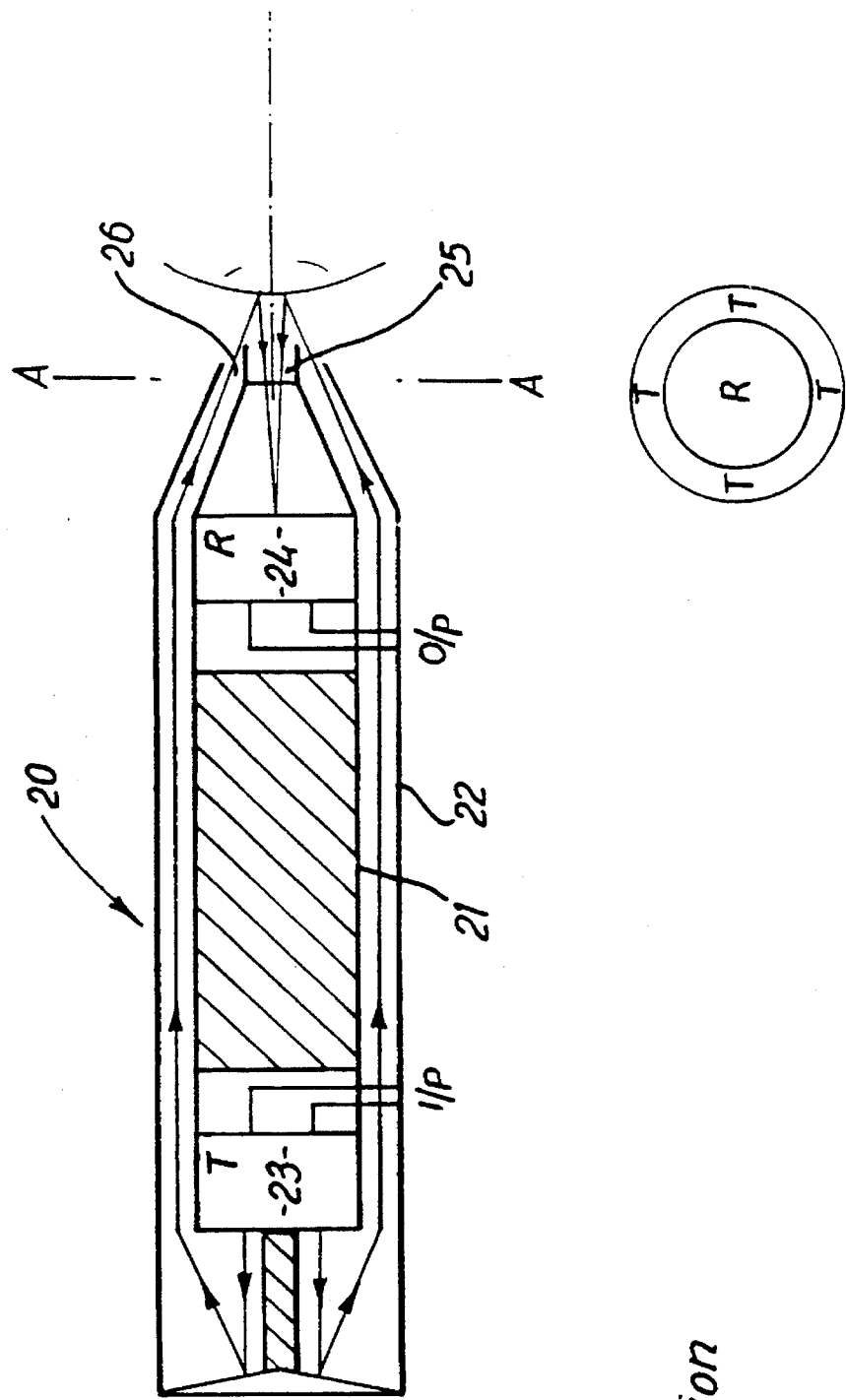
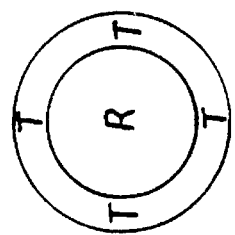
FIG. 5
T Transmission
R Reception

TONOMETER

This invention relates to a tonometer for measuring Iintra-ocular pressure.

Tonometry is the common procedure for measuring the Intra-ocular pressure of the eye. Many known tonometric assessments require the use of anaesthesia and contact with the eye or a short blast of high pressure air to be directed at the eye. These known methods cause a sensation in the eye resulting in discomfort to the patient. What is more contact with the eye may result in abrasion and cross infection. Repeated mesurements comprising contact with the eye also have a massaging effect on the eye which may adversely affect the accuracy of subsequent measurements.

U.S. Pat. Nos. 4,945,913 and 4,930,507 describe tonometers for determining the Intra-ocular pressure of an eye in which the eye is dynamically sealed within a chamber and the pressure of the chamber is measured as a frequency range of sound waves are directed at the eye. The resonant response of the eye, which is related to the Intra-ocular pressure, will have a direct effect on the overall resonant response of the system. The change in pressure in the chamber is related to the resonant response of the system. The dynamic seal, which is essential if chamber pressure is to be measured accurately, is difficult to achieve as the apparatus is placed in direct contact with the face. This contact is found to be disconcerting by many patients.

U.S. Pat. No. 4,928,697 describes a tonometer for determining the Intra-ocular pressure of an eye in which high and low frequency sound waves are directed toward the cornea and reflected therefrom. The output signals created by amplitude modulation of the reflected sound waves are directly related to the Intra-ocular pressure of the eye. The wave source must be located a fixed distance from the eye and this is achieved by the patient placing his head adjacent a chin and forehead support. This may be uncomfortable for the patient.

The present invention has been made from a consideration of these problems.

According to a first aspect of the present invention there is provided a tonometer for measuring the Intra-ocular pressure of an eye comprising an emitter for emitting a signal towards the eye, a receiver for receiving the signal on being reflected from the eye, and a monitoring device for monitoring the amplitude of the signal received by the receiver, wherein in use the emitter and/or receiver is/are in motion relative to the eye while the monitoring device is operating, the monitoring device comprising means for taking and/or storing a measurement wherein the distance between the eye and the receiver is such that substantially the strongest signal is received.

According to a second aspect of the present invention there is provided a method of monitoring the Intra-ocular pressure of an eye, comprising transmitting a signal from a transmitter towards the eye, using a receiver to collect the signal reflected from the eye and monitoring the amplitude of the collected signal, wherein the emitter and/or receiver is/are moved relative to the eye while the monitoring device is operating, the monitoring device comprising means for taking and/or storing a measurement when the distance between the eye and the receiver is such that substantially the strongest signal is received.

The signal preferably comprises an ultrasound wave, that is a wave having a higher frequency than those detectable by the human ear. For example, 40 KHz waves are suitable, although other frequencies may well be appropriate.

The monitoring device is preferably an osciloscope or meter such as a voltmeter. The means for taking and/or storing a measurement takes the measurement when the signal is at its strongest, for example a peak hold facility could be employed.

It has been found preferable to arrange the transmitter and receiver in a twin walled housing, the part of the housing which collects the received signal extending beyond the part of the housing via which the transmitted signal exits the housing, the said parts being arranged in a concentric manner so as to minimise errors induced through non perpendicular approach of the apparatus head to the patient.

Furthermore the part of the housing for collecting the received signal preferably extends beyond the part of the housing via which the transmitted signal exists so as to eliminate the very high signal received when the head of the apparatus is in virtual contact with the eye surface.

The apparatus and method of the present invention provide accurate results without providing an uncomfortable sensation in the eye as no contact need be made with the eye. No anaesthetic is necessary and the apparatus does not require a skilled operator. The apparatus of the present invention should facilitate self determination of Intra-ocular pressure. The apparatus of the present invention can be handheld, is readily portable and may be battery operated if necessary.

In order that the present invention may be more readily understood a specific embodiment thereof will now be described by way of example only with reference to the accompanying drawings in which:

FIG. 2 is a schematic illustration of the tonometer of FIG. 1;

FIG. 3 shows the tonometer head of FIG. 2;

FIG. 4 is a callibration plot for the apparatus FIG. 1 in which the measured voltage may be used to give an indication of Intra-ocular pressure;

FIG. 5 shows a longitudinal sectional view through tonometer head in accordance with the invention.

Figure 1:
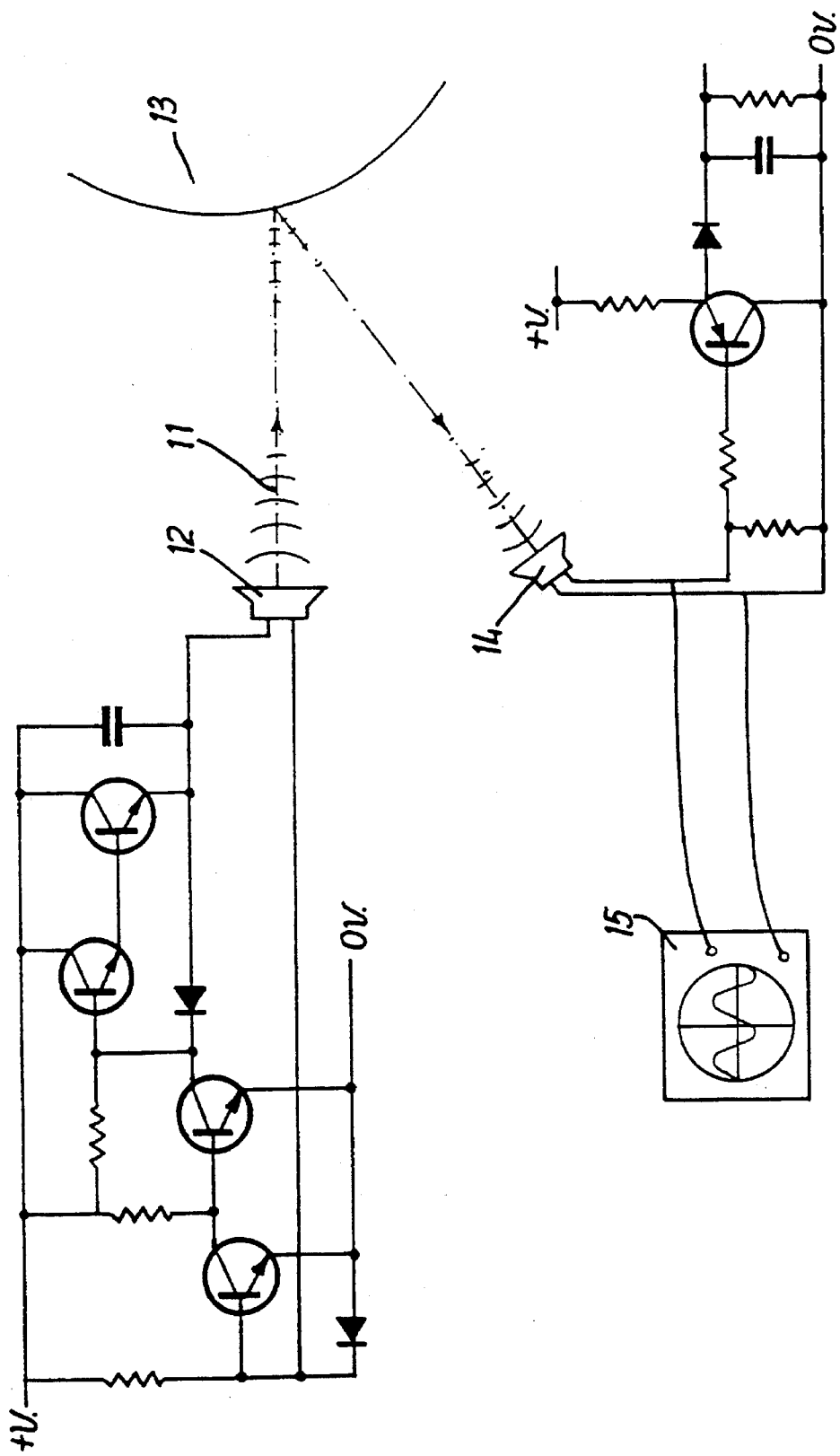
FIG. 1 is a schematic illustration of one tonometer in accordance with the present invention.

Referring to FIGS. 1 to 3 an electric circuit produces a stable 40 Khz ultrasound wave 11 which is used to drive an emitter 12 from an oscillating high frequency electronic signal. The ultrasound waves are directed at the eye 13 from the emitter 12. The ultrasound waves are subsequently reflected from the corneal surface of the eye 13 and are then collected by a receiver 14. The receiver 14 is connected to a monitoring apparatus 15 such as an osciloscope or after appropriate amplification and rectification the returning signal can be assessed. The amplitude of the soundwaves arriving at the receiver may be analysed by way of the monitoring apparatus.

By utilising a "Peak Holding" meter it is possible to "search and find" the location where the reflected signal is at its strongest and thus record and store the potential difference measured when the receiver is in that location. Prior to storage the signal reflected and amplified in order to facilitate calibration and accurate measurement of the Intra-ocular pressure.

The measured signal on the monitoring apparatus 15 bears a direct relationship to the rigidity of the eye and in turn to the Intra-ocular pressure of the eye. FIG. 4 shows a callibration graph of mV as measured by an osciloscope or voltmeter using the apparatus of the present invention against the Intra-ocular pressure of the eye (mmHg) measured by another method. Thus a measurement by the apparatus of the present invention can be used to give the Intra-ocular pressure of the eye using the callibration graph or other means.

With reference to FIG. 5 the tonometer head 20 comprises concentrically arranged inner and outer tubes 21, 22. The transmitter 23 and receiver 24 are mounted in the inner tube 21. Concentric apertures 25, 26 are provided at the right end of the tubes as illustrated. Here the inner receiver tube 21 extends beyond the outer transmitter tube 22.

In use the transmitter 23 transmits a wave which passes between the inner and outer tubes and is reflected by the eye into the inner receiver tubes 21 and receiver 24 located therein.

Figure 6:
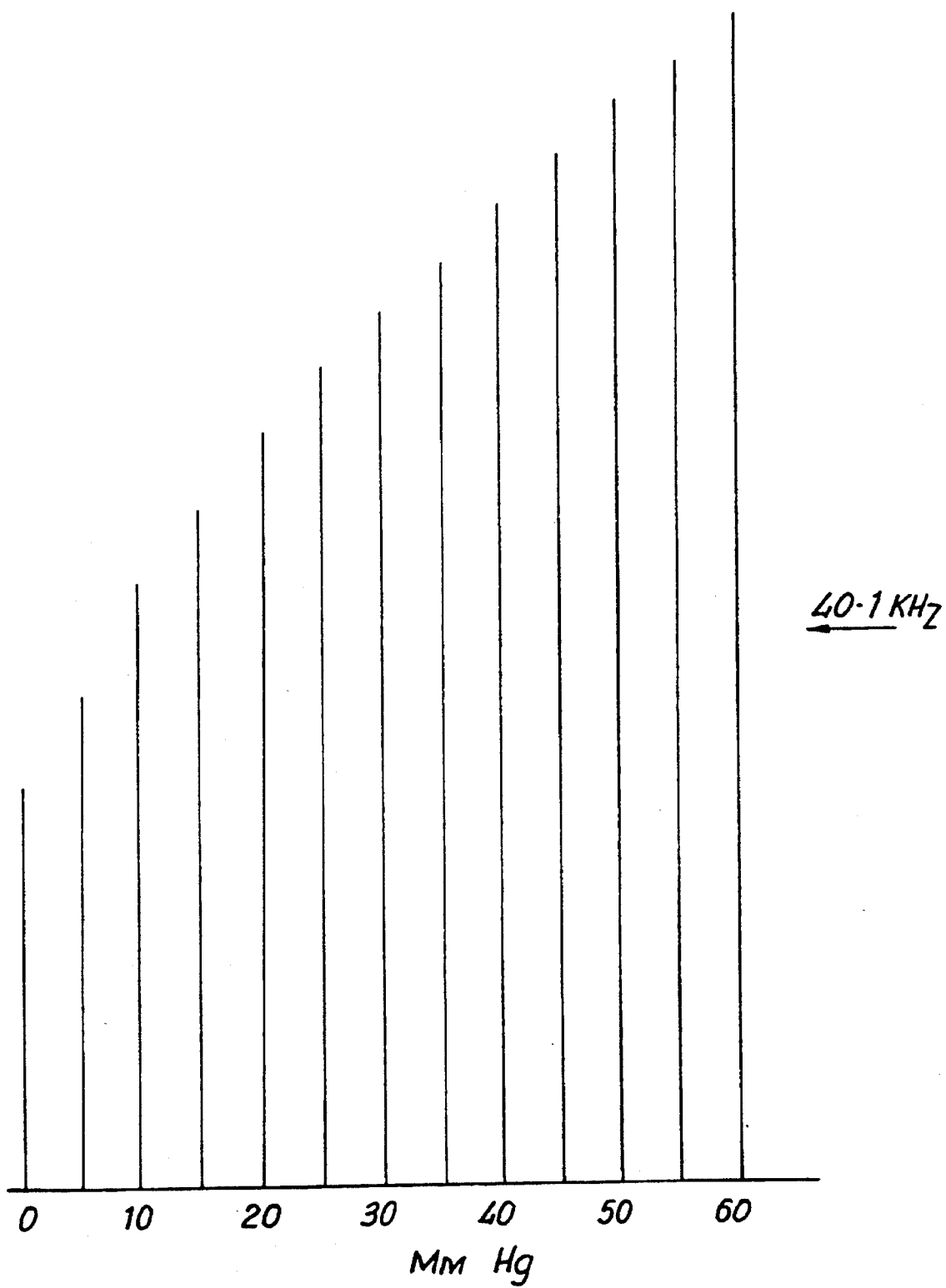
FIG. 6 shows the results of an experiment to establish the relationship between Intra-ocular pressure and the amplitude of the reflected ultrasonic sound of pig eyes.

With reference to FIG. 6 an experiment was designed whereby the Intra-ocular pressure within a pig eye could be pneumatically raised and recorded, whilst at the same time the ultrasonic reflection was also monitored, the point of greatest amplitude being permanently recorded as a voltage on a voltmeter with peak hold facility.

In order to detect the very small variations in amplitude and thereby signal variations that occur with small increases in intra-ocular pressure it was necessary to amplify the output from the probe. A 20× gain was used during the experiment. The majority of this signal was then offset to allow the use of the most sensitive microvolt in the volt meter.

Using the above technique it was possible to obtain the results shown in FIG. 6 which clearly indicate that a predictable relationship exists between Intra-ocular pressure and the amplitude of the reflected ultrasonic sound from the cornea. Thus by accurately assessing the amplitude of corneal ultrasonic reflection we can determine the Intra-ocular pressure without any ocular intrusion of sensation.

It is to be understood that the embodiment described herein has been described by way of illustration only. Many modifications and variations are possible within the scope of the claims. For example, with reference to FIG. 5 the waves emitted by the transmitter need not be reflected from the rear surface of the apparatus. The transmitter can be arranged to emit the waves towards the front of the apparatus.

I claim:

1. A tonometer for measuring the Intra-ocular pressure of an eye comprising an emitter for emitting a primary signal towards the cornea of the eye, a receiver for receiving the primary signal on being reflected from the cornea, the amplitude of the primary signal being altered on reflection from the cornea, the changes to the amplitude of the primary signal depending on the rigidity of the cornea, and a monitoring device for monitoring the peak-to-peak amplitude of the reflected primary signal received by the receiver, wherein the emitter and/or receiver is movable relative to the eye while the monitoring device is operating, the monitoring device comprising means for taking and/or storing a measurement when the distance between the eye and the receiver is such that substantially the largest peak-to-peak amplitude of the primary reflected signal is received, the measurement being calibrated to provide the Intra-ocular pressure of the eye.

2. A tonometer as claimed in claim 1, wherein the signal comprises an ultrasound wave.

3. A tonometer as claimed in claim 1, wherein the frequency of the signal is substantially 40 KHz.

4. A tonometer as claimed in claim 1, wherein the means for taking and/or storing a measurement takes the measurement when the strongest signal is emitted.

5. A method of monitoring the Intra-ocular pressure of an eye comprising the steps of:

directing a primary signal towards the cornea of the eye with an emitter;

collecting the primary signal reflected from the cornea with a receiver, the amplitude of the primary signal being altered on reflection from the cornea, the changes to the amplitude of the primary signal depending on the rigidity of the cornea;

monitoring the amplitude of the reflected primary signal with a monitoring device, wherein the emitter and/or receiver is moved relative to the eye while the monitoring device is operating, the monitoring device comprising means for taking and/or storing a measurement when the distance between the eye and the receiver is such that substantially the largest peak-to-peak amplitude of the primary reflected signal is received; and calibrating the measurement to provide the Intra-ocular pressure of the eye.

6. A method as claimed in claim 5, wherein the emitter and/or receiver is not columnated.

* * * * *